US00PP24122P2

(12) United States Plant Patent
Lannes

(10) Patent No.: US PP24,122 P2
(45) Date of Patent: Dec. 31, 2013

(54) ***MANDEVILLA* PLANT NAMED 'LANNEVADA'**

(50) Latin Name: *Mandevilla sanderi*
Varietal Denomination: Lannevada

(75) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 106 days.

(21) Appl. No.: 13/374,928

(22) Filed: Jan. 23, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

(56) References Cited

PUBLICATIONS

Pluto Upov Plant Variety Database 201301, retrieved on Jun. 26, 2013, retrieved from the Internet at <http://www.upov.int/pluto/en/index.jsp> for *Mandevilla* 'Lannevada', one page.*

* cited by examiner

*Primary Examiner* — June Hwu
(74) *Attorney, Agent, or Firm* — C. A. Whealy

(57) ABSTRACT

A new and distinct cultivar of *Mandevilla* plant named 'Lannevada', characterized by its trailing plant habit; moderately vigorous growth habit; glossy dark green-colored leaves; early flowering habit; and red-colored flowers.

2 Drawing Sheets

Botanical designation: *Mandevilla sanderi.*
Cultivar denomination: 'LANNEVADA'.

BACKGROUND OF THE INVENTION

The present invention relates to a new and distinct cultivar of *Mandevilla* plant, botanically known as *Mandevilla sanderi* and hereinafter referred to by the name 'Lannevada'.

The new *Mandevilla* plant is a product of a planned breeding program conducted by the Inventor in Malause, France. The objective of the breeding program is to create new trailing *Mandevilla* plants with red-colored flowers.

The new *Mandevilla* plant originated from a cross-pollination conducted by the Inventor in Malause, France on Sep. 22, 2006 of *Mandevilla sanderi* 'Sunmanderemi', disclosed in U.S. Plant Pat. No. 16,449, as the female, or seed parent with a proprietary selection of *Mandevilla sanderi* identified as code number 05-075-22, not patented, as the male, or pollen, parent. The new *Mandevilla* plant was discovered and selected by the Inventor as a single flowering plant from within the progeny of the stated cross-pollination in a controlled greenhouse environment in Malause, France in May, 2008.

Asexual reproduction of the new *Mandevilla* plant by cuttings in a controlled greenhouse environment in Malause, France, since May, 2010 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Lannevada'. These characteristics in combination distinguish 'Lannevada' as a new and distinct *Mandevilla* plant:

1. Trailing plant habit.
2. Moderately vigorous growth habit.
3. Glossy dark green-colored leaves.
4. Early flowering habit.
5. Red-colored flowers.

Plants of the new *Mandevilla* can be compared to plants of the female parent, 'Sunmanderemi'. Plants of the new *Mandevilla* differ primarily from plants of 'Sunmanderemi' in the following characteristics:

1. Leaves of plants of the new *Mandevilla* are flatter and thicker than leaves of plants of 'Sunmanderemi'.
2. Plants of the new *Mandevilla* and 'Sunmanderemi' differ slightly in flower color.
3. Flowers of plants of the new *Mandevilla* are resistant to sun fading whereas flowers of plants of 'Sunmanderemi' are not resistant to sun fading.

Plants of the new *Mandevilla* can be compared to plants of the male parent selection. Plants of the new *Mandevilla* differ primarily from plants of the male parent selection in the following characteristics:

1. Leaves of plants of the new *Mandevilla* are flatter and thicker than leaves of plants of the male parent selection.
2. Plants of the new *Mandevilla* and the male parent selection differ in flower color as plants of the male parent selection have pink-colored flowers.
3. Flowers of plants of the new *Mandevilla* are resistant to sun fading whereas flowers of plants of the male parent selection are not resistant to sun fading.

Plants of the new *Mandevilla* can also be compared to plants of *Mandevilla sanderi* 'Sherry', not patented. In side-by-side comparisons conducted in Malause, France, plants of the new *Mandevilla* differed from plants 'Sherry' in the following characteristics:

1. Plants of the new *Mandevilla* were more trailing than and not as upright as plants of 'Sherry'.
2. Plants of the new *Mandevilla* were more vigorous than plants of 'Sherry'.
3. Plants of the new *Mandevilla* flowered two weeks earlier than plants of 'Sherry'.
4. Plants of the new *Mandevilla* had darker-colored flowers than plants of 'Sherry'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lannevada' grown in a container.

The photograph on the second sheet is a close-up view of a typical flowering plant of 'Lannevada'.

DETAILED BOTANICAL DESCRIPTION

The aforementioned photographs and following observations, measurements and values describe plants grown during the autumn in two-liter containers in polyethylene-covered greenhouse in Malause, France and under cultural practices typical of *Mandevilla* commercial production. During the production of the plants, day temperatures ranged from 8° C. to 26° C. and night temperatures ranged from 3° C. to 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla sanderi* 'Lannevada'.

Parentage:

*Female, or seed, parent.*—*Mandevilla sanderi* 'Sunmanderemi', disclosed in U.S. Plant Pat. No. 16,449.

*Male, or pollen, parent.*—Proprietary selection of *Mandevilla sanderi* identified as code number 05-075-22, not patented.

Propagation:

*Type.*—By vegetative cuttings.

*Time to initiate roots, summer.*—About two weeks at 23° C. to 25° C.

*Time to initiate roots, winter.*—About three weeks at 23° C. to 25° C.

*Time to produce a rooted young plant, summer.*—About five to six weeks at 23° C. to 25° C.

*Time to produce a rooted young plant, winter.*—About six to eight weeks at 23° C. to 25° C.

*Root description.*—Fibrous, fine; light yellowish white in color.

*Rooting habit.*—Freely branching; medium density.

Plant description:

*Plant and growth habit.*—Trailing plant habit; upright and outwardly spreading; broad inverted triangle in shape; moderately vigorous growth habit.

*Plant height.*—About 28.4 cm.

*Plant diameter (spread).*—About 29.9 cm.

*Lateral branch description.*—Branching habit: Moderately freely branching habit with about five lateral branches developing per plant; pinching enhances lateral branch development. Length: About 12.1 cm. Diameter: About 2.5 mm. Internode length: About 2 cm. Strength: Strong. Texture: Smooth, glabrous. Color: Close to 144B; older stems, close to N199B.

Foliage description:

*Arrangement.*—Opposite, simple.

*Length.*—About 5.4 cm.

*Width.*—About 3.7 cm.

*Shape.*—Ovate to obovate.

*Apex.*—Abruptly acute.

*Base.*—Truncate to obtuse.

*Margin.*—Entire.

*Texture, upper and lower surfaces.*—Smooth, glabrous; glossy.

*Venation pattern.*—Pinnate, reticulate.

*Color.*—Developing leaves, upper surface: Darker than between 143A and 146A. Developing leaves, lower surface: Close to 146A. Full expanded leaves, upper surface: Between N137A and 147A; venation, close to 143B to 143C. Fully expanded leaves, lower surface: Close to 147B; venation, close to 145C.

*Petiole length.*—About 1.4 cm.

*Petiole diameter.*—About 1 mm.

*Petiole texture, upper and lower surfaces.*—Smooth, glabrous.

*Petiole color, upper surface.*—Close to 144B.

*Petiole color, lower surface.*—Close to 145B.

Flower description:

*Flower type and flowering habit.*—Single salverform flowers arranged in axillary racemes; flowers star-shaped and face upright and outwardly; about three flowers developing per inflorescence and about 15 flowers developing per plant.

*Natural flowering season.*—Early flowering habit with plants begin to flower about six weeks after planting; plants flower continuously from summer into the autumn in France.

*Flower longevity on the plant.*—About seven days; flowers not persistent.

*Fragrance.*—Not detected.

*Flowers.*—Appearance: Flared trumpet, corolla fused and five-parted. Diameter: About 8.1 cm. Depth (length): About 6.4 cm. Tube length: About 5 cm.

*Flower buds.*—Length: About 4.6 cm. Diameter: About 8 mm. Shape: Narrowly obovate. Color: Close to 145B; towards the base, close to 144B.

*Corolla.*—Quantity and arrangement: Five petals arranged in a single whorl and fused at the base. Petal lobe length: About 4.1 cm. Petal lobe width: About 3.5 cm. Petal shape and appearance: Roughly spatulate; lower 55% of the petal is fused. Petal apex: Acute. Petal margin: Entire; slightly undulate. Petal texture, upper and lower surfaces: Smooth, glabrous; velvety. Throat texture: Smooth, glabrous. Tube texture: Smooth, glabrous. Color: Petal, when opening, upper surface: More intense than 46A to 46B; throat, close to 24A, towards the base of the throat, close to 31A to 31B. Petal, when opening, lower surface: Close to 53A; tube, close to 54A, towards the base of the tube, close to 150B and 34B. Petal, fully opened, upper surface: Close to 45A to 45B and 46B, towards the apex, close to 46A; throat, close to N25B, towards the base of the throat, close to 31A to 31B; with development, color becoming closer to 53A. Petal, fully opened, lower surface: Close to 53A to 53B; tube, close to 54A, towards the base of the tube, close to 150B and 34B. Sepals: Quantity and arrangement: Five sepals arranged in a single whorl. Sepal length: About 8 mm. Sepal width: About 2 mm. Sepal shape: Lanceolate. Sepal apex: Narrowly acuminate. Sepal base: Roughly truncate. Sepal margin: Entire. Sepal texture, upper and lower surfaces: Smooth, glabrous. Sepal color: Immature, upper and lower surfaces: Close to 145B; towards the apex, close to 151A and towards the base, close to 144C. Mature, upper and lower surfaces: Close to 145B; towards the apex, close to 151A and towards the base, close to 144C.

*Peduncles.*—Length: About 6.3 cm. Diameter: About 2 mm. Texture: Smooth, glabrous. Strength: Flexible, but strong. Color: Close to 144B.

*Pedicels.*—Length: About 1.5 cm. Diameter: About 1.5 mm. Texture: Smooth, glabrous. Strength: Flexible, but strong. Color: Close to 144C.

*Reproductive organs.*—Stamens: Quantity and arrangement: Typically five; basifixed; anthers connivent. Filament length: About 1 mm. Anther shape: Ellipsoidal. Anther length: About 8 mm. Anther color: Close to 160B. Pollen amount: None observed. Pistils: Quantity: Typically one. Pistil length: About 2 cm. Style length: About 1.8 cm. Style color: Close to 144D. Stigma shape: Conical. Stigma color: Close to 144B. Ovary color: Close to 144C.

*Seeds and fruits.*—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lannevada' as illustrated and described.

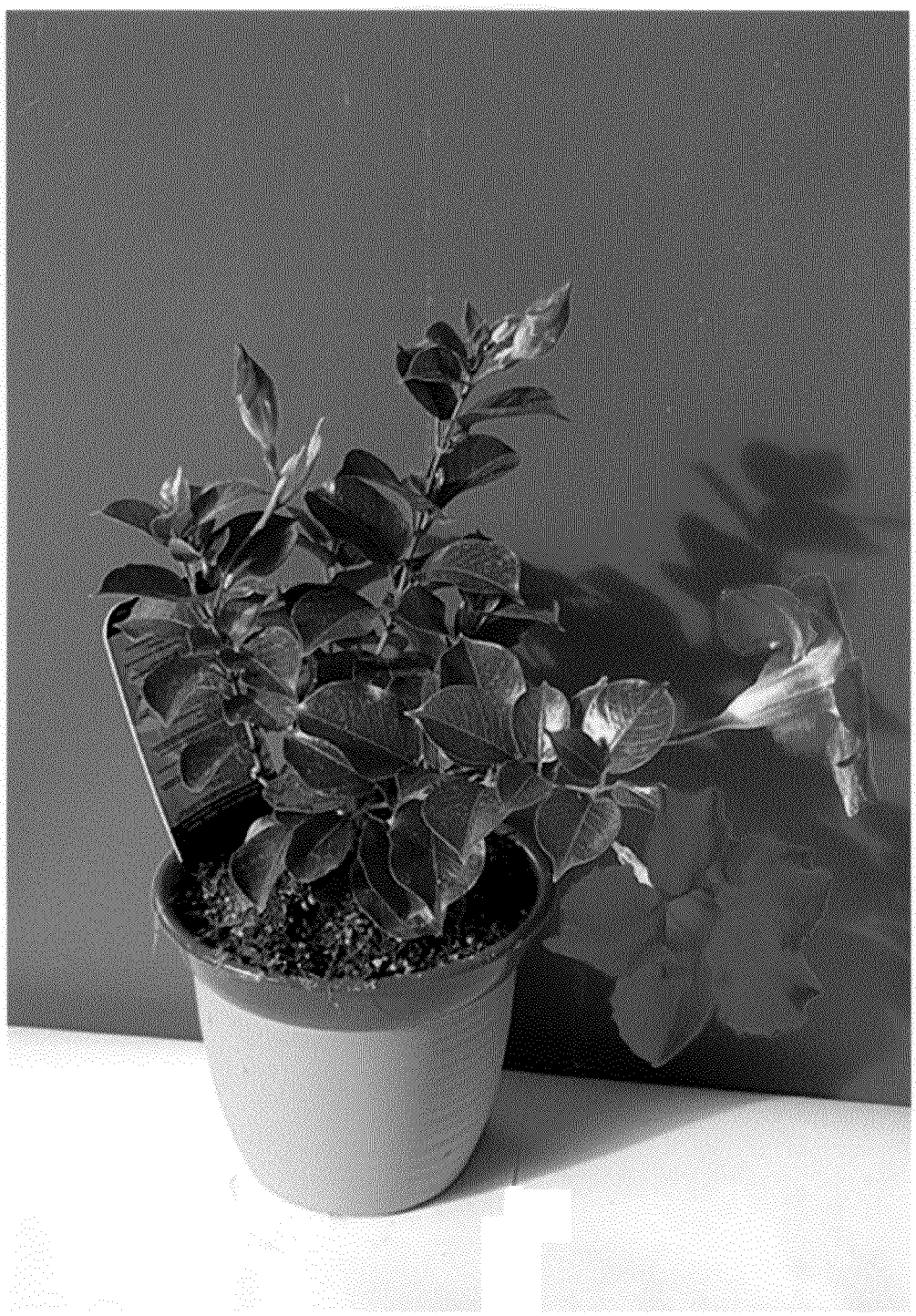

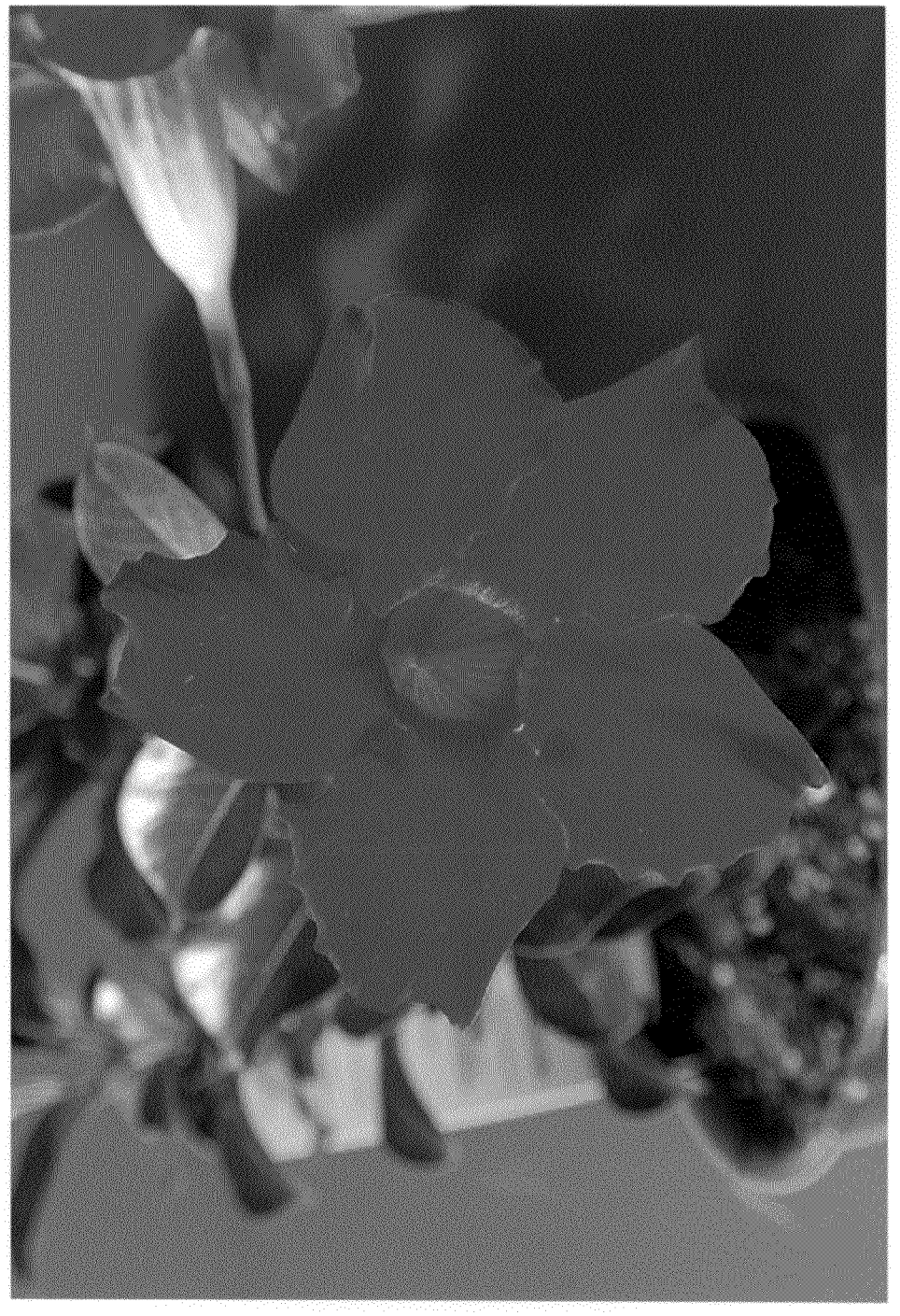

* * * * *